US010751322B2

(12) United States Patent
Romani et al.

(10) Patent No.: US 10,751,322 B2
(45) Date of Patent: Aug. 25, 2020

(54) INDOLE-3-ALDEHYDE FOR TREATING DYSREACTIVE IMMUNE DISORDERS

(71) Applicant: Universita' degli Studi di Perugia, Perugia (IT)

(72) Inventors: Luigina Romani, Perugia (IT); Paolo Puccetti, Perugia (IT); Teresa Zelante, Perugia (IT); Maurizio Ricci, Perugia (IT); Stefano Giovagnoli, Perugia (IT)

(73) Assignee: Universita' degli Studi di Perugia, Perugia (IT)

( * ) Notice: Subject to any disclaimer, the term of this patent is extended or adjusted under 35 U.S.C. 154(b) by 0 days.

(21) Appl. No.: 14/913,382

(22) PCT Filed: Aug. 18, 2014

(86) PCT No.: PCT/IB2014/063953
§ 371 (c)(1),
(2) Date: Feb. 22, 2016

(87) PCT Pub. No.: WO2015/025259
PCT Pub. Date: Feb. 26, 2015

(65) Prior Publication Data
US 2016/0206595 A1   Jul. 21, 2016

(30) Foreign Application Priority Data
Aug. 22, 2013 (IT) .............................. MO2013A0241

(51) Int. Cl.
*A61K 31/404* (2006.01)
*A61K 35/747* (2015.01)
*A61K 45/06* (2006.01)
*A61K 35/74* (2015.01)

(52) U.S. Cl.
CPC ............ *A61K 31/404* (2013.01); *A61K 35/74* (2013.01); *A61K 35/747* (2013.01); *A61K 45/06* (2013.01)

(58) Field of Classification Search
None
See application file for complete search history.

(56) References Cited

U.S. PATENT DOCUMENTS

2011/0002891 A1* 1/2011 Minbiole ............... A61K 35/74
424/93.4

FOREIGN PATENT DOCUMENTS

| CN | 101406497 | 4/2009 |
|---|---|---|
| WO | WO 2015/025259 | 2/2015 |

OTHER PUBLICATIONS

Nakajima et al., "Isolation and identification of lateral bud growth inhibitor, indole-3-aldehyde, involved in apical dominance of pea seedlings", Phytochemistry 2002, vol. 61, pp. 863-865.*
Hendrickson et al., Remington: The Science and Practice of Pharmacy, 21st Ed., Chapters 21 and 39; Lippincott Williams & Wilkins: Philadelphia, PA. (Year: 2005).*
International Search Report and the Written Opinion dated Nov. 19, 2014 From the International Searching Authority Re. Application No. PCT/IB2014/063953 and Its Translation Into English.
Yang et al. "Metabolism Studies of Indole Derivatives Using a Staurosporine Producer, Streptomyces Stauroporeus", Journal of Natural products, XP055116636, 60(1): 44-48, 1997. Abstract, p. 44, col. 1-col. 2, Para 1, Compound 6.
Zelante et al. "Tryptophan Catabolites From Microbiota Engage Aryl Hydrocarbon Receptor and Balance Mucosal Reactivity Via Interleukin-22", Immunity, XP055116601, 39(2): 372-385, Aug. 22, 2013. Abstract.
Zhou et al. "Anti-Inflammatory Effects of Caper (*Capparis spinosa* L.) Fruit Aqueous Extract and the Isolation of Main Phytochemicals", Journal of Agricultural and Food Chemistry, XP055116611, 58(24): 12717-12721, Published on Web Nov. 24, 2010, p. 12720, col. 1, Para 4-col. 2, Para 1, Abstract, Compound.
Kerley-Hamilton et al. "Obesity is Mediated by Differential Aryl Hydrocarbon Receptor Signaling in Mice Fed a Western Diet", Environmental Health Perspectives, 120(9): 1252-1259, Published Online May 18, 2012.
Quintana "Regulation of Central Nervous System Autoimmunity by the Aryl Hydrocarbon Receptor", Seminars in Immunopathology, 35(6): 627-635, Published Online Sep. 3, 2013.
Oliva et al. "Randomised Clinical Trial: The Effectiveness of Lactobacillus Reuteri ATCC 55730 Rectal Enema in Children With Active Distal Ulcerative Colitis", AP&T Alimentary Pharmacology and Therapeutics, XP055130426, 35(3): 327-334, Published Online Dec. 8, 2011.
Romani et al. "Microbiota Control of a Tryptophan-AhR Pathway in Disease Tolerance to Fungi", European Journal of Immunology, XP055505520, 44(11): 3192-3200, Published Online Oct. 20, 2014.

* cited by examiner

*Primary Examiner* — Michelle F. Paguio Frising

(57) ABSTRACT

The therapeutic use of bacteria, specifically but not only lactobacilli, which produce indole-3-aldehyde, or directly of indole-3-aldehyde itself, is proposed as a means of prevention and treatment of immune dysreactive disorders in which the hyper-inflammatory or autoimmune component represents the basic element.

3 Claims, 2 Drawing Sheets

INDOLE-3-ALDEHYDE FOR TREATING DYSREACTIVE IMMUNE DISORDERS

RELATED APPLICATIONS

This application is a National Phase of PCT Patent Application No. PCT/IB2014/063953 having International filing date of Aug. 18, 2014, which claims the benefit of priority of Italian Patent Application No. MO2013A000241 filed on Aug. 22, 2013. The contents of the above applications are all incorporated by reference as if fully set forth herein in their entirety.

FIELD AND BACKGROUND OF THE INVENTION

This invention relates to the use of indole-3-aldehyde for treating immune dysreactive disorders, in particular of inflammatory and infectious diseases.

A large number of human diseases recognizes immune dysreactivity as a pathogenetic element which is exemplified, inter alia, in forms of acute and chronic hyper-inflammation (e.g., rheumatic ailments) and in autoimmune forms, i.e., activation of aberrant responses towards components of the human organism [1]. In many cases, the control of immune dysreactivity is purely symptomatic (e.g., as regards inflammatory disorders, by means of non-steroid anti-inflammatory drugs). This represents a serious therapeutic problem because it requires long-term treatments which can produce a series of, sometimes serious, side effects. As regards autoimmune forms, the functional meiopragia of the organ (e.g., the pancreas in type I diabetes) requires a costly daily substitutive therapy which strongly restricts the quality of the patient's life.

It is therefore of paramount importance to develop new treatment methods based on drugs that act with alternative mechanisms with respect to the mere control of symptoms and which interrupt the pathogenetic mechanisms, reversing or at least controlling the expression of the illness in the long term [2].

The growing understanding of the pathogenetic factors of many human illnesses, of both an infective and an inflammatory nature, permits foreseeing pathogenetic, if not etiologic operations, of the molecular type, aimed at optimizing the results of current therapies. The invention concerns the use of molecules, either endogenous or exogenous, that allow achieving this result.

In this direction, inventors have for some time been studying the possible transcriptional control of "anti-inflammatory" genes, i.e., which codify for endogenous proteins that permit immune homeostasis and therefore appear deficient or malfunctioning wherever an immune dysreactivity condition arises [3], [4].

Among the candidate genes that attract most attention is a group of genes regulated transcriptionally by a transcription factor known as receptor of aryl hydrocarbons, commonly known as AhR (acronym of Aryl Hydrocarbon Receptor) [5]. This transcription factor was initially identified as target and mediator of the activity of one of the most toxic xenobiotics, dioxin, but it has also shown itself capable of regulating the cell differentiation of a lymphocyte T population (regulator T cells) whose main function is precisely to control immune hyperactivity, including inflammation and autoimmunity [6].

The AhR is technically regulated by the ligand: in other words, in order to activate itself as transcriptional regulator, it must "encounter" molecules generally coming from the outside of the cell, often even of a xenobiotic nature.

Taking into consideration this group of genes, the inventors interested themselves in studying the role of the bacteria present in the intestine (and not only) of human beings (collectively known by the term Microbiota) in determining the state of health and illness, and more specifically, the role of such bacteria in infections and inflammatory disorders of the gastrointestinal tract.

The intestinal microbiota consists of hundreds of different bacterial species whose numerous metabolic activities affect the state of health. In fact, the intestinal microbiota takes part in the metabolism of carbohydrates, proteins and lipids, and regulates the secretion of hormones and the pH, as well as the production of compounds with anti-bacterial and immune modulation action [8], [9]. During the course of the evolution of the human species, an important and delicate balance has been created of mutual benefit to human beings and microflora, which however risks being compromised by sudden changes. In conditions of psycho-physical, food and environment stress, or after taking drugs, we assist in an imbalance of the microflora (dysbiosis) that makes the body susceptible to infections and illnesses such as obesity, intestinal inflammation (e.g., Crohn's disease and necrotizing entrocolitis) and tumours. Various factors influence the activities of intestinal microbiota, in both a positive and negative sense. Among these we can recall immune system tolerance, enzyme synthesis to use available nutrients, stress resistance, eating habits, antibiotic therapy, the host's genetic situation and chronic illnesses.

More in particular, the course of studies and experiments which have led to the invention are the following.

Studies in metagenomics (aimed at identifying quantity and quality of bacterial species) and metabolomics (aimed at identifying the bacterial metabolites produced) in the stomach and faeces of suitably selected mice have led to the discovery that commensal bacteria of the mouse and human intestine, in particular those known as lactobacilli, produce a new possible AhR ligand belonging to the family of indolic derivatives of the tryptophan metabolism. This is indole-3-aldehyde or indole-3-carbaldehyde (IAld, MF: C9H7NO, name IUPAC: IH-indole-3-carbaldehyde), the formula of which is shown below:

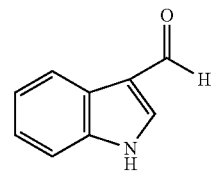 [SMILES: O=Cc1c[nH]c2ccccc12]

The identification of this new ligand was achieved starting with the knowledge of the fact that the endogen metabolites of tryptophan, which is a "food" of both human beings and their microbes, play a major role in the immunity homeostasis of the intestine of mammals, and with the consideration that, among the various metabolic paths used by intestinal bacteria, that of indolics seemed the most probable, taking into account the type of bacterium (i.e., lactobacilli) which were expanded in the intestine in conditions of abundance of tryptophan.

It is also underlined that, even though many AhR activator ligands are known belonging both to the animal and vegetable world [7], a ligand has never, on the other hand, been described which, originating from the prokaryotes, has functional activities in mammals, including therefore human beings.

This new possible AhR ligand having been identified, tests were performed to determine its capacity to effectively act as such. Such tests showed that the IAld appeared to have an agonist activity comparable or superior to that of other indolic ligands also deriving from the metabolism of the tryptophan, such as indole-3-acetaldehyde (IAAld), indole-3-acetic acid (IAA, Indole Acetic Acid), indole-3-lactic acid (ILA, Indole Lactic Acid), and have also shown that the AhR-agonist activity strictly depended on the dose. This has made it possible to come to the conclusion that IAld is in fact the prototype ligand of prokaryote origin that can interact with the AhR of the guest of mammals, including human beings.

A next step was aimed at understanding whether the interaction between IAld and AhR was functionally active. For this purpose, the transcription was assessed of genes usually transcribed following AhR activation. The examined genes included detoxification genes (in particular Cyp1A1 and CypB1) and codifying genes for proteins of an enzymatic or cytochemical nature, the translational potential of which is known in the field of the above-mentioned pathologies (anti-inflammatory genes), in particular IL-10 (interleuchin 10), IL-22 (interleuchin 22), IDO1 (Indole-ammine 2,3-dioxygenase 1) [8-10]. This evaluation has made it possible to determine that IAld produces, in a dose-dependent way, both the activation of the considered detoxification genes, above all in the colon, and, very important, the activation of the anti-inflammation genes both in the colon and in the stomach. It has therefore been demonstrated that IAld is able to "naturally" activate anti-inflammatory genes, i.e., which modulate the dysreactive process in its pathogenesis instead of only in its symptomatic expression, as is the case with current anti-inflammatory non-steroid drugs.

As the last step, the therapeutic potential of IAld was tested, by using experimental mice models in which the inflammatory dysreactive component was well known. For this purpose, experimental infection models were used from *Candida albicans* (which, as is known, is a commensal fungus of the oro-gastrointestinal tract, of the vagina and of the skin), whose inflammatory dysreactivity pathogenetic role is known, and a colitis model more frankly tied to an inflammatory/immunity dysregulation which involves, in this case too, IL-22, IL-10 and IDO1 [14],[15]. The data obtained from these experimental models showed that:
  i) IAld was able to significantly reduce the growth of *Candida albicans* and that the therapeutic effect could not be found in the absence of AhR;
  ii) at the same time, IAld produced, again in a way dependent on the presence of AhR, IL-22 and IL-10 in the examined infection models;
  iii) a protective effect was also found in mice with colitis.

The experimental results, which will be illustrated in greater detail later on, have therefore provided evidence that a protective mechanism implemented through the IAld/AhR/IL-22/IL-10 axis can be therapeutically useful in conditions of immune dysreactivity, distinguished by excessive inflammation and reduced immunologic tolerance.

Consequently, according to a first aspect of the invention, the use is proposed of indole-3-aldehyde in the medical field, in particular as a means of prevention and treatment for immune dysreactive disorders in those cases where the hyper-inflammatory component represents the basic element.

SUMMARY OF THE INVENTION

The IAld can be used directly as such, or can be produced by bacteria belonging to the microbiota of the human intestine, in particular, but not only, lactobacilli.

According to another aspect of the invention, a pharmaceutical composition is provided comprising IAld as the active principle, present directly in the composition or produced by bacteria belonging to the microbiota of the human intestine, in particular lactobacilli, eventually in combination with one or more adjuvants and/or excipients pharmaceutically acceptable.

According to a further aspect of the invention, the use is proposed of the above pharmaceutical composition for the preparation of a medication, in particular for treating immune dysreactive disorders in which the hyper-inflammatory component represents the basic element.

In detail, examples of these disorders are:
  intestinal dysbiosis and resulting associated immune disorders which are, for example, food intolerances and in general metabolic disorders;
  colitis and other intestinal chronic diseases;
  intestinal bacterial and protozoal infectious diseases with mucosal involvement;
  mucosal and vaginal candidiasis;
  mucositis in course of radiotherapy and chemotherapy in patients with cancer and transplant patients;
  psoriasis.

BRIEF DESCRIPTION OF THE SEVERAL VIEWS OF THE DRAWINGS

The experimental results summarized above will now be illustrated in greater detail, with reference to the attached drawings, wherein.

DESCRIPTION OF SPECIFIC EMBODIMENTS OF THE INVENTION

As has been said above, once IAld has been identified as possible AhR ligand of interest, the next step in experimental activity consists in testing the capacity of IAld to act in that guise.

Figure 1:
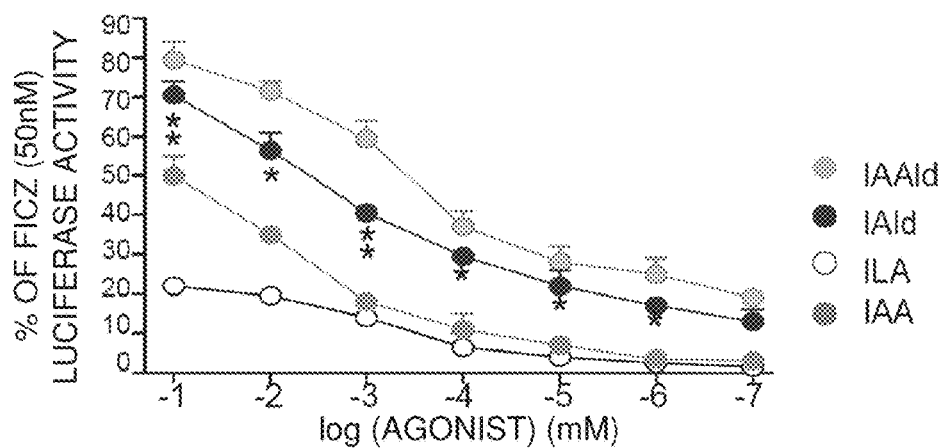
FIG. 1 is a graph comparing the capacity of the indole-3-aldehyde and of a certain number of other metabolites of tryptophan to act as AhR ligands.

For this test, an AhR-responsive cell line was stimulated (cell line H1L1.1c2 containing a luciferase of firefly sensitive to stably transfected AhR) with IAld, indole-3-acetaldehyde (IAAld), indole-3-acetic acid (IAA) and indole-3-lactic acid (ILA). In a way well known to the technician in the field, the agonist activity was determined by means of luciferase test, and in FIG. 1 the luciferase activity of the different ligands, representative of such agonist activity, has been indicated, on the ordinate, as a percentage of the response induced by 50 nM of formylindolo[3,2-b]carbazole (FICZ) according to the ligand dose, expressed in logarithmic scale on the abscissa. The figure shows that the AhR-agonist activity of IAld is substantially comparable to that of IAAld and is superior to that of ILA and IAA. The illustration also shows that the AhR-agonist activity is closely dependent on the dose.

Figure 2:
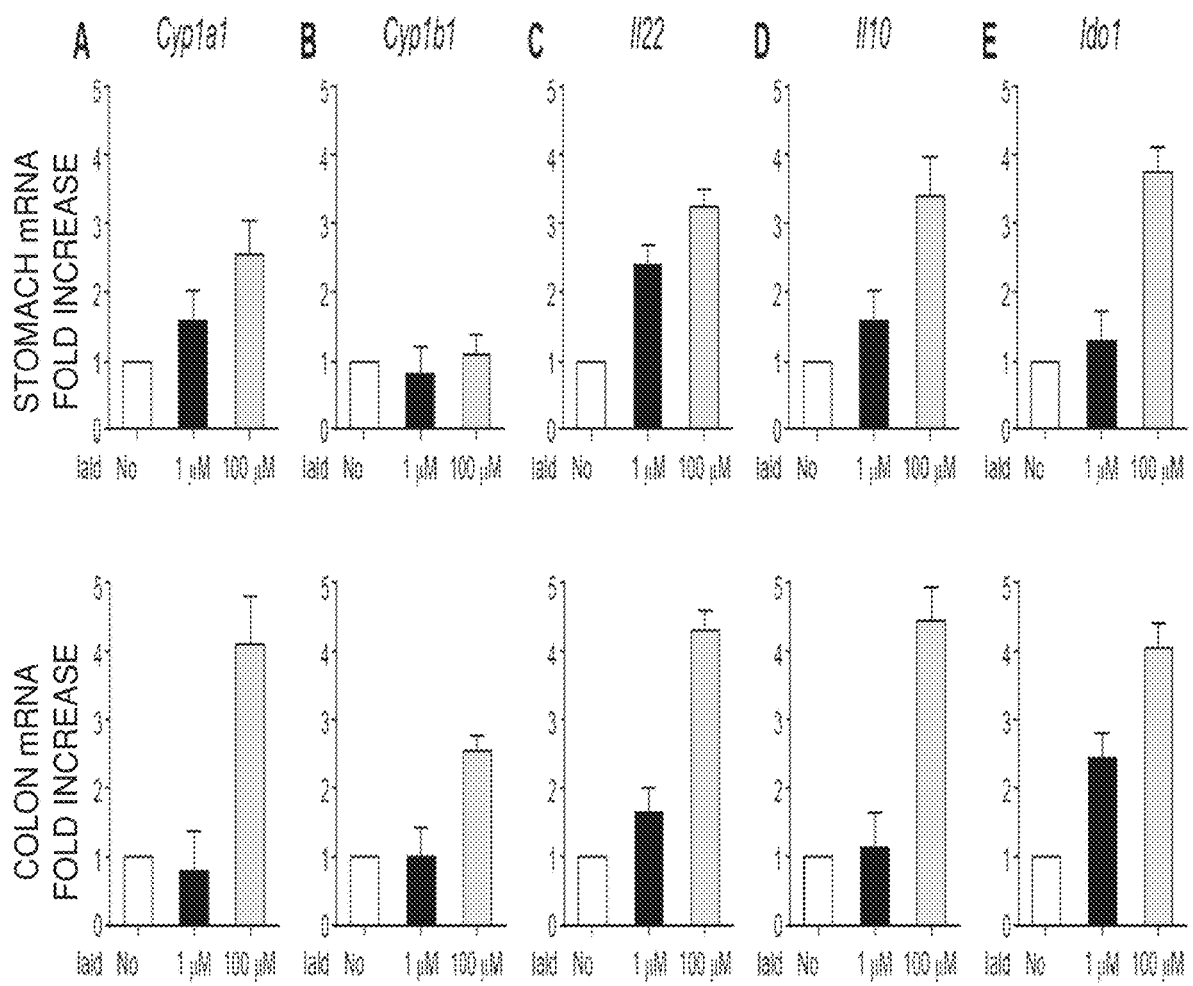
FIG. 2 shows the results of the verifications of the capacity of the indole-3-aldehyde to activate detoxificating and anti-inflammatory genes.

FIG. 2 shows the results of the verifications of the capacity of the IAld to activate detoxificating genes, and precisely Cyp1A1 and Cyp1B1, and anti-inflammation genes. The latter includes, as we have said:
- IL-22 (interleuchin 22), taken into consideration for its epithelium-protective activity;
- IL-10 (interleuchin 10), taken into consideration for its strong anti-inflammatory activity; and
- IDO1 (Indoleamine 2,3-dioxygenase), which is the key enzyme of immunologic tolerance.

Figure 3:
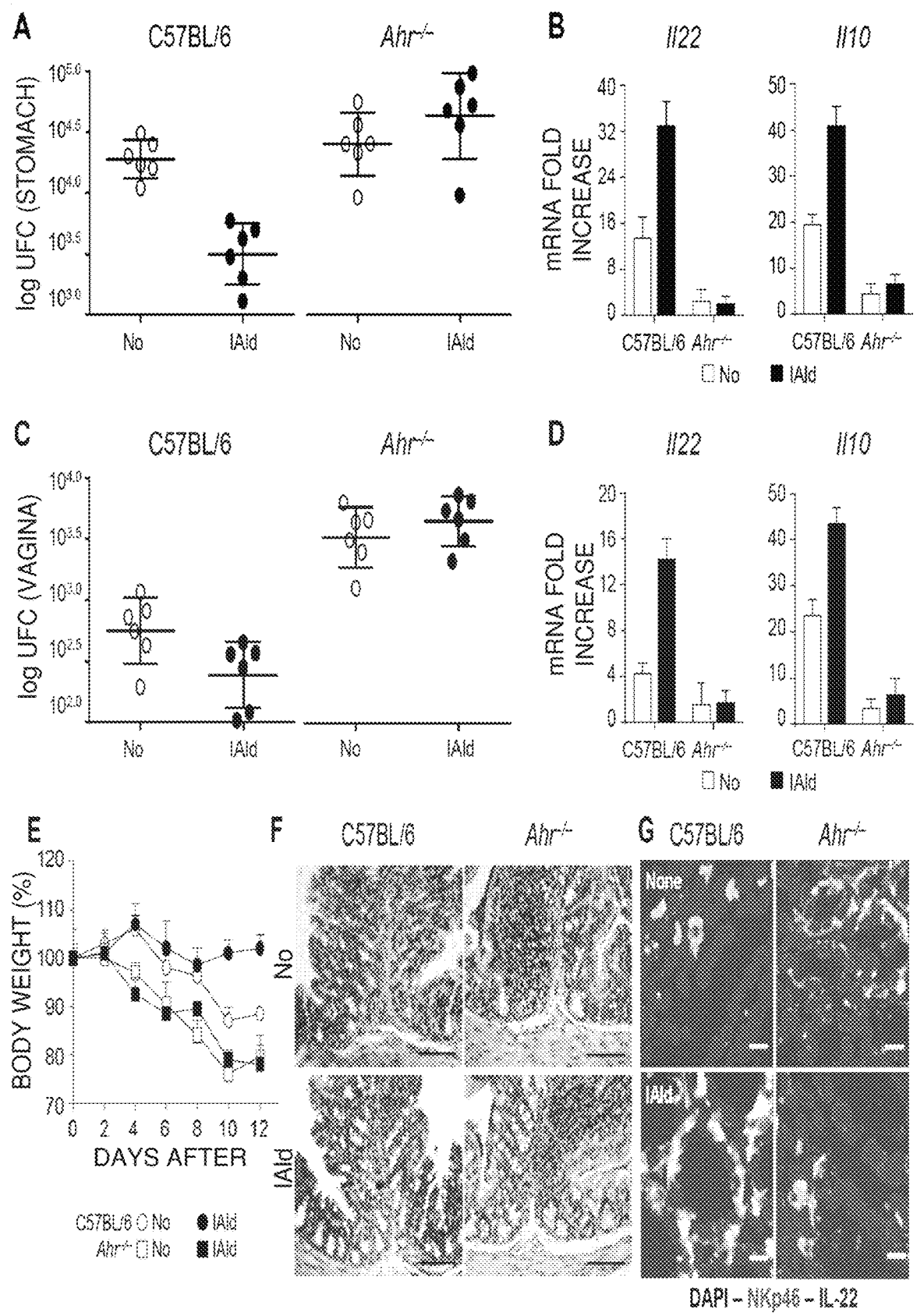
FIG. 3 shows the results of the verifications of the therapeutic effect of the indole-3-aldehyde.

For these verifications, cultures were set up of mice stomachs and colons stimulated with 1 or 100 mM of IAld for 24 hours in vitro before determining the transcription of the above indicated genes by means of polymerase reaction. The histograms A-E show the activation (expressed in terms of the number of times the mRNA increases) of the genes Cyp1A1, Cyp1B1, IL-22, IL-10 and IDO1 respectively in the stomach (top diagram) and in the colon (bottom diagram) as a consequence of the stimulation. Particularly evident is the activation of Cyp1A1 in the colon and, very important, the activation of IL-22, IL-10 and IDO1 in both organs. For comparison, also indicated are the values in the absence of stimulation with IAld. As can be seen, and as has been said above, the results of the activation are strongly dependent on the dose of IAld. Finally, FIG. 3 shows the results of the assessment of the therapeutic effect of IAld in treating candidiasis and colitis. To assess the therapeutic effect in treating candidiasis, two experimental models were used of infection by *C. albicans* obtained by administration of the fungus intragastrically (by means of a tube) and intravaginally (by means of tip) respectively. To assess the therapeutic effect in treating colitis, the model used requires the administration of an irritant (dextran sodium sulphate, DDS), through the mouth. The assessment was made on mice C57BL/6 and on mice AhR$^{-/-}$, i.e., mice from which the AhR receptor had been artificially removed. The treatment with IAld lasted for 7 days. Preliminary experiments in which IAld was administered in different doses and using different ways of administration suggested that the IAld could be successfully administrated intragastrically with a dose of 18 mg/kg, daily, during the entire period of the experiment.

FIG. 3 clearly shows:
a) for mice infected with *Candida albicans*:
- a significant reduction in growth (usually expressed in terms of number of colony forming units, CFU) of *Candida albicans* at stomach level (diagram A) and vagina level (diagram C);
- the contemporaneous activation of IL-22 and IL-10 both in the stomach (histogram B) and in the vagina (histogram B);

b) for mice with colitis:
- the protective effect in terms of prevention of the reduction in body weight (graph E, showing the percentage variation in body weight according to the duration of the administration of DSS, in days);
- the improvement in the degree of tissue inflammation (photographs F, obtained by colon histopathology);
- the expansion of cells producing IL-22 (photographs G, obtained by immunofluorescence).

The diagrams and the photographs in FIG. 3 clearly show that the therapeutic effect is only to be found in mice C57BL/6 and not in mice AhR$^{-/-}$, and is therefore tied to the presence of AhR.

In conclusion, the object of the invention is the therapeutic use of bacteria, specifically but not only lactobacilli, which produce a ligand of AhR, IAld, or directly IAld itself, as a means of prevention and treatment of immune dysreactive disorders in which the hyper-inflammatory or auto-immune component represents the basic element (for example, colitis, psoriasis and other intestinal chronic diseases). Among the target genes that promote the protective effect are codifying ones for proteins of an enzymatic or cytochemical nature (e.g., IDO1, IL-10 and IL-22), the translational potential of which has already been delved into in detail in the field of the above-mentioned disorders. It is therefore reasonable to suppose that IAld may have a therapeutic role in disorders of an infective and/or inflammatory nature wherein the recovery is required:
- of mucous barrier integrity such as during neoplastic cytoreductive therapies as radiotherapy and chemotherapy in transplant patients or in patients with cancer affected by mucositis or intestinal [16] (bacterial and protozoal) infectious diseases with mucosal involvement or in case of psoriasis;
- of the immunologic tolerance and of the consequent restoring of organ functionality in chronic inflammatory disorders of organs and mucous [17], such as intestinal dysbiosis and resulting associated immune disorders which are, for example, food intolerances and in general metabolic disorders;

BIBLIOGRAPHY

1. Tabas, I. & Glass, C. K. Anti-inflammatory therapy in chronic disease: challenges and opportunities. *Science* 339, 166-172 (2013).
2. Fitzpatrick, M. & Young, S. P. Metabolomics—a novel window into inflammatory disease. *Swiss medical weekly* 143 (2013).
3. Belladonna, M. L., Orabona, C., Grohmann, U. & Puccetti, P. TGF-beta and kynurenines as the key to infectious tolerance. *Trends in molecular medicine* 15, 41-49 (2009).
4. Romani, L. & Puccetti, P. Controlling pathogenic inflammation to fungi. *Expert review of anti-infective therapy* 5, 1007-1017 (2007).
5. Quintana, F. J. The aryl hydrocarbon receptor: a molecular pathway for the environmental control of the immune response. *Immunology* 138, 183-189 (2013).
6. Pot, C. Aryl hydrocarbon receptor controls regulatory CD4+ T cell function. *Swiss medical weekly* 142, w13592 (2012).
7. Stejskalova, L., Dvorak, Z. & Pavek, P. Endogenous and exogenous ligands of aryl hydrocarbon receptor: current state of art. *Current drug metabolism* 12, 198-212 (2011).
8. Brestoff, J. R. & Artis, D. Commensal bacteria at the interface of host metabolism and the immune system. *Nature immunology* 14, 676-684 (2013).
9. Robles Alonso, V. & Guarner, F. Linking the gut microbiota to human health. *The British journal of nutrition* 109 Suppl 2, S21-26 (2013).
10. De Luca, A. et al. IL-22 and IDO1 Affect Immunity and Tolerance to Murine and Human Vaginal Candidiasis. *PLoS pathogens* 9, e1003486 (2013).
11. Puccetti, P. & Grohmann, U. IDO and regulatory T cells: a role for reverse signalling and non-canonical NF-kappaB activation. *Nature reviews. Immunology* 7, 817-823 (2007).
12. Romani, L. & Puccetti, P. Protective tolerance to fungi: the role of IL-10 and tryptophan catabolism. *Trends in microbiology* 14, 183-189 (2006).

13. Zelante, T., Iannitti, R., De Luca, A. & Romani, L. IL-22 in antifungal immunity. *European journal of immunology* 41, 270-275 (2011).

14. Asquith, M. & Powrie, F. An innately dangerous balancing act: intestinal homeostasis, inflammation, and colitis-associated cancer. *The Journal of experimental medicine* 207, 1573-1577 (2010).

15. Wang, K., Grivennikov, S. I. & Karin, M. Implications of anti-cytokine therapy in colorectal cancer and autoimmune diseases. *Annals of the rheumatic diseases* 72 Suppl 2, ii100-103 (2013).

16. Sonnenberg, G. F., Fouser, L. A. & Artis, D. Border patrol: regulation of immunity, inflammation and tissue homeostasis at barrier surfaces by IL-22. *Nature immunology* 12, 383-390 (2011).

17. Jager, S., Stange, E. F. & Wehkamp, J. Inflammatory bowel disease: an impaired barrier disease. *Langenbeck's archives of surgery/Deutsche Gesellschaft fur Chirurgie* 398, 1-12 (2013).

What is claimed is:

1. A pharmaceutical composition comprising indole-3-aldehyde as an active ingredient at a dose of 18 mg/kg daily and in combination with one or more adjuvants and/or pharmaceutically acceptable excipients, wherein the composition comprises bacteria producing indole-3-aldehyde, said bacteria is a *Lactobacillus* that belong to the microbiota of human intestines.

2. A method of treatment of immune dysreactive disorders in which the hyper inflammatory component represents the basic element, comprising administering to a patient the pharmaceutical composition according to claim 1.

3. A pharmaceutical composition, comprising, as the active principle, indole-3-aldehyde at a dose of 18 mg/kg daily, the composition is for use in the treatment of immune dysreactive disorders in which the hyper inflammatory component represents the basic element, the composition further comprising *Lactobacillus* producing indole-3-aldehyde.

* * * * *